US012016800B2

(12) United States Patent
Schwarz et al.

(10) Patent No.: US 12,016,800 B2
(45) Date of Patent: Jun. 25, 2024

(54) EYECUP, HEADBAND, AND EYE MASK FOR SLEEPING

(71) Applicant: Manta Sleep LLC, Jackson, WY (US)

(72) Inventors: Benjamin Schwarz, Jackson, WY (US); Mark Zhang, Jackson, WY (US)

(73) Assignee: Manta Sleep LLC, Jackson, WY (US)

( * ) Notice: Subject to any disclaimer, the term of this patent is extended or adjusted under 35 U.S.C. 154(b) by 261 days.

(21) Appl. No.: 17/521,069

(22) Filed: Nov. 8, 2021

(65) Prior Publication Data
US 2023/0062643 A1    Mar. 2, 2023

(30) Foreign Application Priority Data

Sep. 1, 2021  (CN) .......................... 202111018095.6

(51) Int. Cl.
*A61F 9/04*        (2006.01)
(52) U.S. Cl.
CPC ...................................... *A61F 9/04* (2013.01)
(58) Field of Classification Search
CPC ......... A45D 44/002; A61F 9/04; A61F 9/045; A61F 2007/0004
See application file for complete search history.

(56) References Cited

U.S. PATENT DOCUMENTS

| | | | | |
|---|---|---|---|---|
| 1,926,926 A | * | 9/1933 | Whitman | A45D 44/22 2/15 |
| 4,243,041 A | * | 1/1981 | Paul | A61F 7/10 351/124 |
| 4,872,217 A | * | 10/1989 | Kitayama | A61F 9/04 2/15 |
| 5,700,238 A | * | 12/1997 | Hyson | A61F 13/124 604/303 |

(Continued)

FOREIGN PATENT DOCUMENTS

| | | |
|---|---|---|
| DE | 202008003814 U1 | 10/2008 |
| KR | 940026207 U | 12/1994 |

(Continued)

OTHER PUBLICATIONS

Combined Search and Examination Report under Sections 17 and 18(3) for related GB Application No. GB2116017.1 dated Jun. 21, 2022, 10 pages.

(Continued)

*Primary Examiner* — F Griffin Hall
(74) *Attorney, Agent, or Firm* — Brad J. Thorson; DeWitt LLP

(57) ABSTRACT

An eye mask for sleeping has a headband and two eyecups. The headband comprises an inner surface and an outer surface. The two eyecups are configured to cover two eyes respectively. Each eyecup has an adhering surface, a contact surface, and multiple first passages. The adhering surface is securely mounted on the inner surface of the headband. The contact surface is configured to cover one of the eyes of the user. The first passages are formed through each eyecup and extend from the adhering surface to the contact surface. With the eyecups mounted on the headband and configured to cover the eyes of the user, because the first passages are formed through the eyecups, heat and moisture can be dissipated and drained via the first passages.

9 Claims, 7 Drawing Sheets

(56) References Cited

U.S. PATENT DOCUMENTS

| | | | |
|---|---|---|---|
| 7,707,655 B2 * | 5/2010 | Braunecker | A61F 7/03 2/206 |
| 8,272,071 B2 * | 9/2012 | Kaiser | A63B 33/004 2/440 |
| 10,383,386 B2 | 8/2019 | Abraham | |
| D861,771 S * | 10/2019 | Schwarz | A61F 9/04 D16/301 |
| 10,960,226 B1 * | 3/2021 | Shulko | A61F 9/04 |
| D923,186 S * | 6/2021 | Guo | D24/206 |
| D954,793 S * | 6/2022 | Schwarz | D16/301 |
| 2003/0056281 A1 * | 3/2003 | Hasegawa | A61N 2/002 2/206 |
| 2006/0157064 A1 * | 7/2006 | Davison | A61F 9/029 128/858 |
| 2010/0122398 A1 | 5/2010 | Luciano | |
| 2014/0331383 A1 * | 11/2014 | Bially | A61F 9/04 2/173 |
| 2016/0008175 A1 * | 1/2016 | Bergman | A61F 9/04 2/171.2 |
| 2019/0110927 A1 * | 4/2019 | Schwarz | A61F 9/04 |
| 2019/0133827 A1 * | 5/2019 | Carver | A61F 9/04 |
| 2022/0304865 A1 * | 9/2022 | Ho | B33Y 80/00 |
| 2023/0000188 A1 * | 1/2023 | Dubois | A61F 9/04 |

FOREIGN PATENT DOCUMENTS

| | | |
|---|---|---|
| KR | 20130012377 A | 2/2013 |
| WO | 2020231343 | 11/2020 |

OTHER PUBLICATIONS

European Search Report for related EPC application No. 21206856 dated Apr. 4, 2022, 8 pages.

* cited by examiner

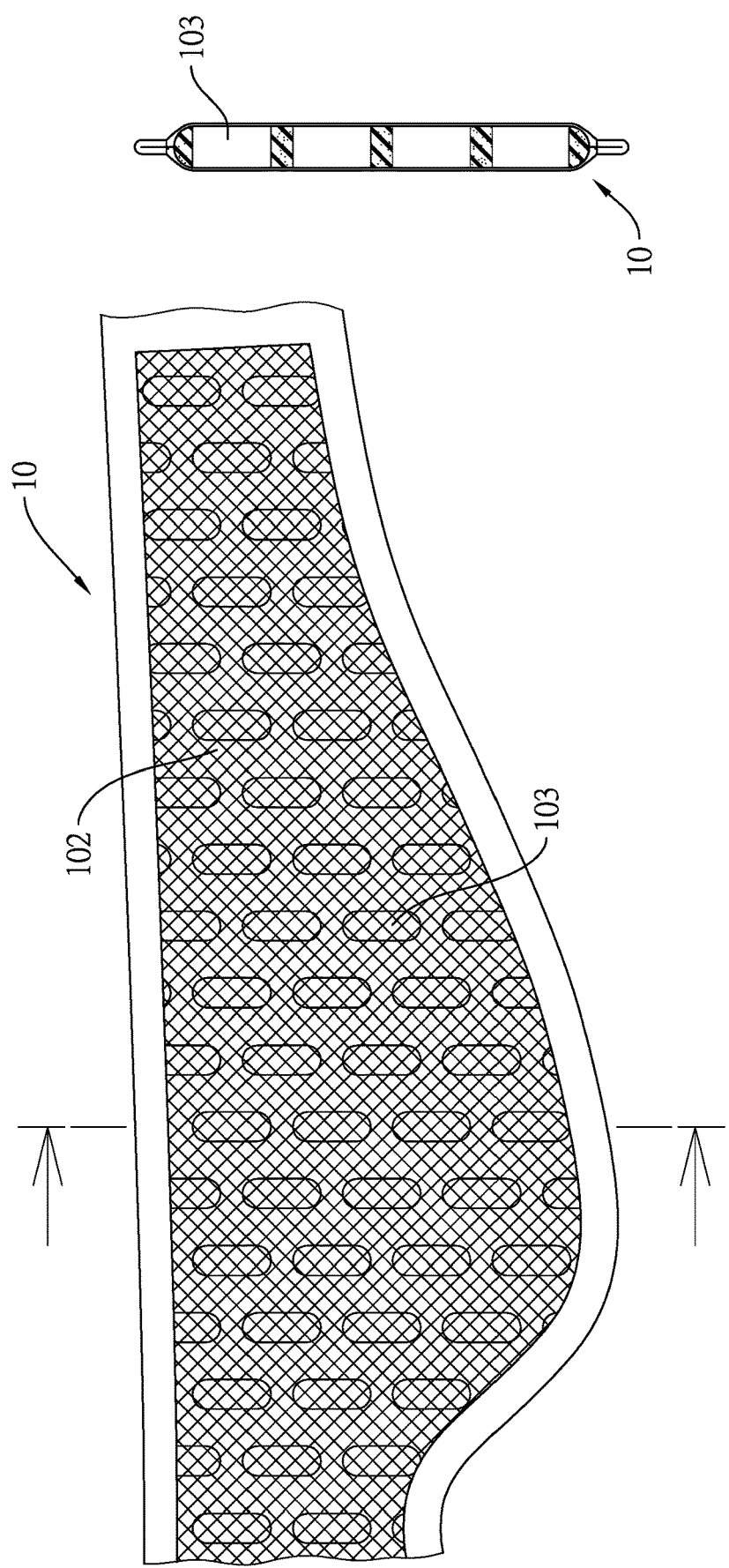

EYECUP, HEADBAND, AND EYE MASK FOR SLEEPING

BACKGROUND OF THE INVENTION

1. Field of the Invention

The present invention relates to an article for daily use, especially to an eye mask that shades light.

2. Description of the Prior Arts

An eye mask is a daily necessity configured to cover eyes and prevents the covered eyes from damage by glare. If the brightness of the environment is high, it will easily affect the sleep quality and even make many people struggle to fall asleep. Therefore, an eye mask worn during sleep for shading light from the environment becomes an important apparatus to maintain the sleep quality. However, even during sleep, the human body's metabolism is still going on continuously, so the body is still constantly excreting sweat.

The conventional eye mask may be made of fabric material. To shade the light from the environment, the density of the fabric material is high, so the effect of absorbing moisture and sweat is poor. In other words, after the user wakes up, the portion of the face covered by the eye mask may have sweat accumulating, which is uncomfortable and may cause skin lesions such as eczema after long-term use.

To overcome the shortcomings, the present invention provides an eyecup and an eye mask with said eyecup to mitigate or obviate the aforementioned problems.

SUMMARY OF THE INVENTION

The main objective of the present invention is to provide an eyecup and an eye mask that can absorb moisture and drain sweat, which provides a comfortable experience for the user.

The eye mask has a headband and two eyecups. The headband has an inner surface and an outer surface. The two eyecups are configured to respectively cover two eyes of a user.

Each one of the eyecup has an adhering surface, a contact surface, and a plurality of first passages. The adhering surface is securely mounted on the inner surface of the headband. The contact surface is configured to cover one of the eyes of the user. The first passages are formed through the eyecup and extending from the adhering surface to the contact surface.

The headband has an inner surface, an outer surface, and a plurality of second passages formed through the headband and extending from the inner surface to the outer surface.

Consequently, the two eyecups are mounted on the headband and configured to cover the eyes of the user. With the first passages formed through the breathable cushion, the heat and moisture can be dissipated and drained via the first passages, which decreases the chance of sweat accumulation between the skin and the eye mask.

Other objectives, advantages and novel features of the invention will become more apparent from the following detailed description when taken in conjunction with the accompanying drawings.

BRIEF DESCRIPTION OF THE DRAWINGS

FIG. 7 is a front elevation view of a headband of the eye mask in FIG. 1;

FIG. 8 is a cross-sectional view of the headband in FIG. 7; and

DETAILED DESCRIPTION OF THE PREFERRED EMBODIMENTS

Figure 1:
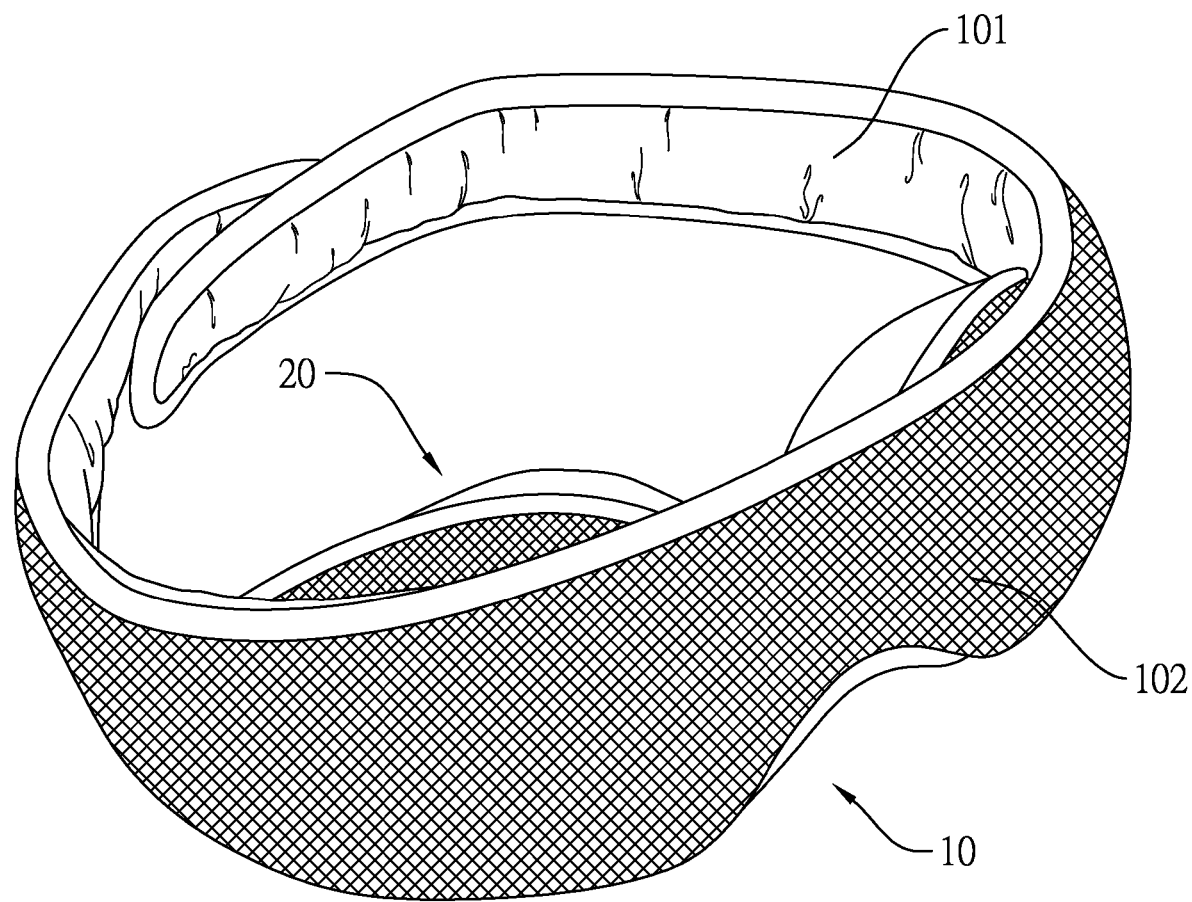
FIG. 1 is a perspective view of an eye mask in accordance with the present invention.
Figure 2:
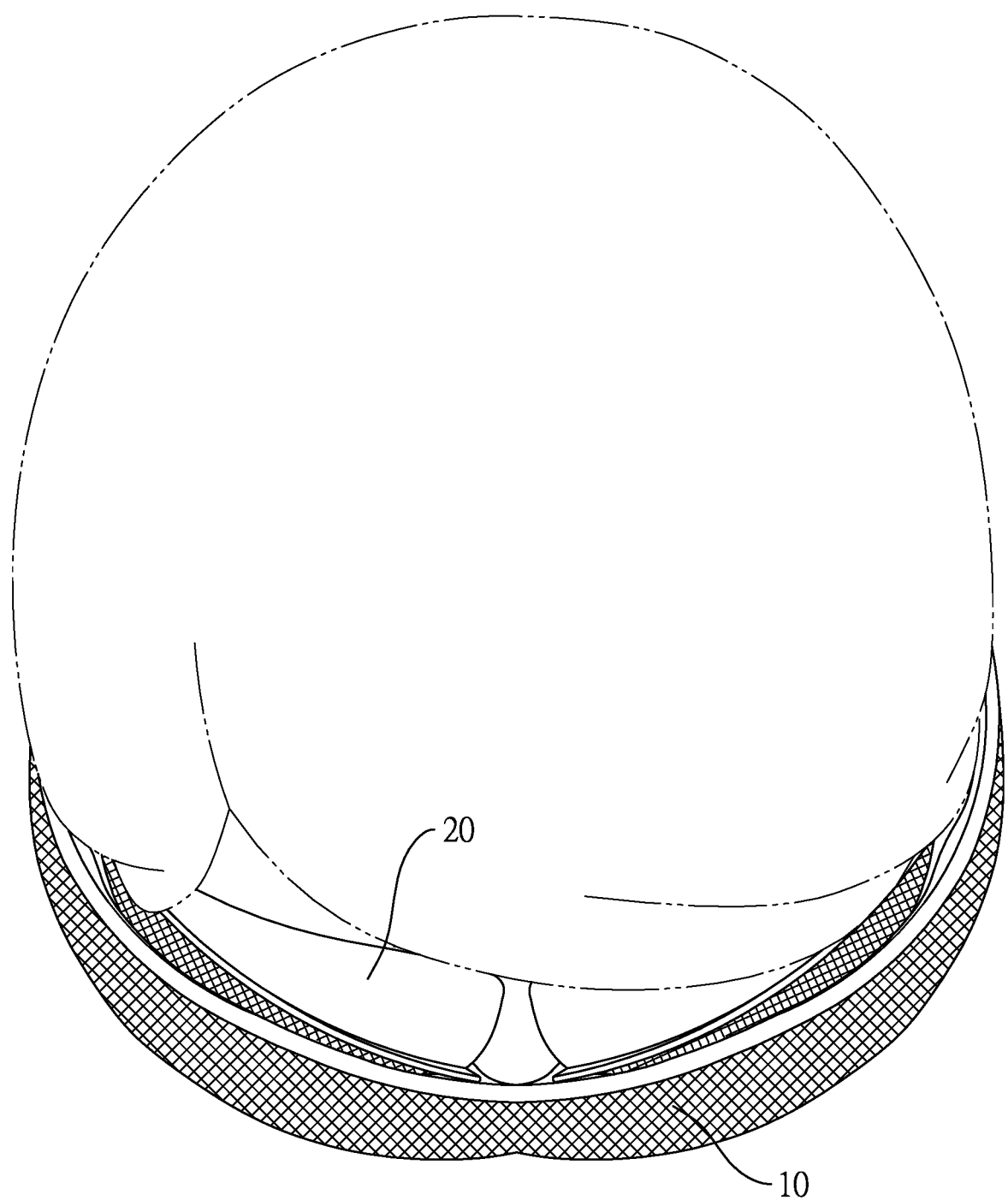
FIG. 2 is a top plan view of the eye mask in FIG. 1, shown in a state of use worn by a user.
Figure 3:
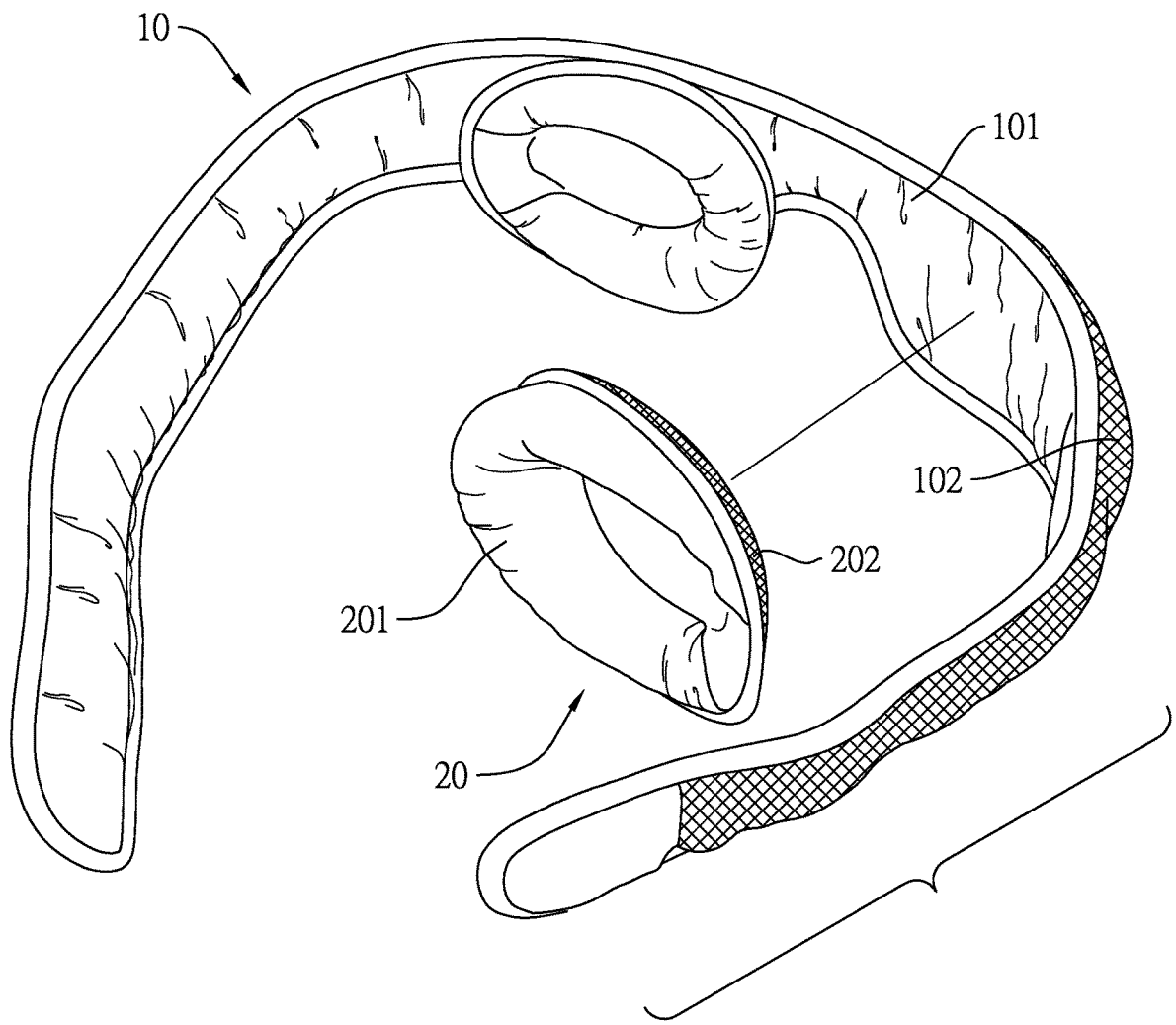
FIG. 3 is an exploded view of the eye mask in FIG. 1.
Figure 4:
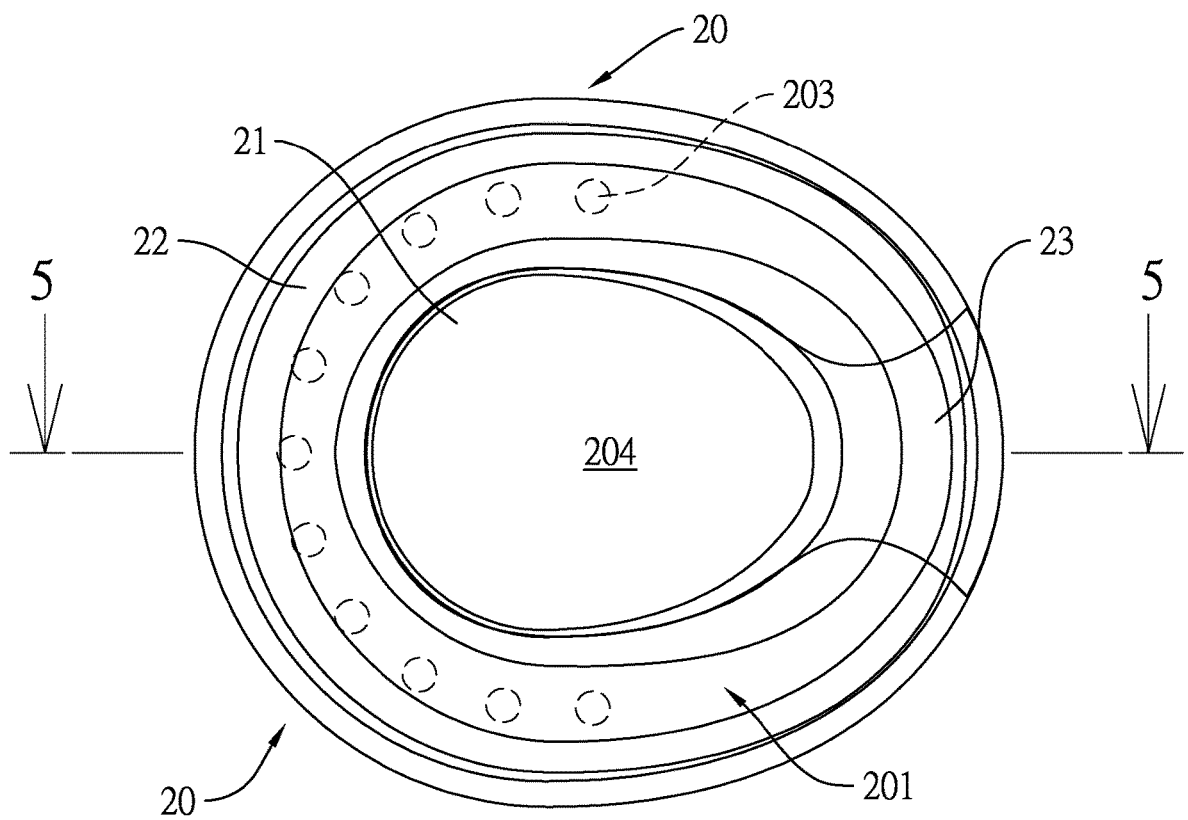
FIG. 4 is a rear elevation view of an eyecup of the eye mask in FIG. 1.
Figure 5:
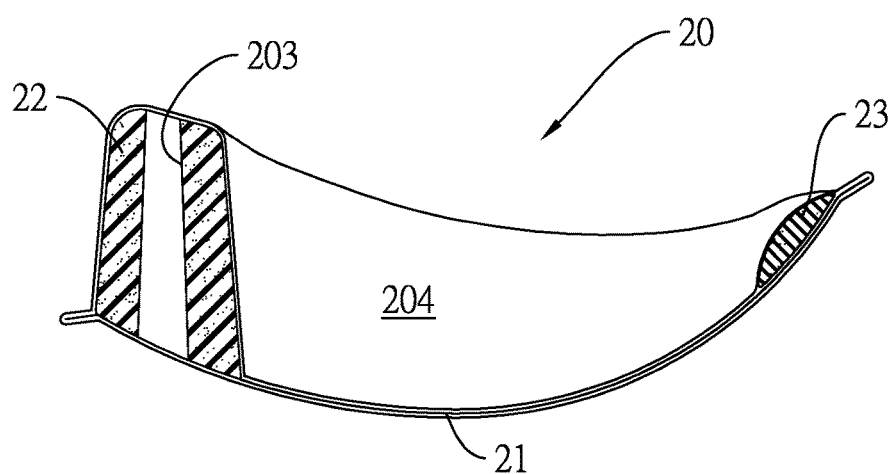
FIG. 5 is a cross-sectional view of the eyecup in FIG. 4.
Figure 6:
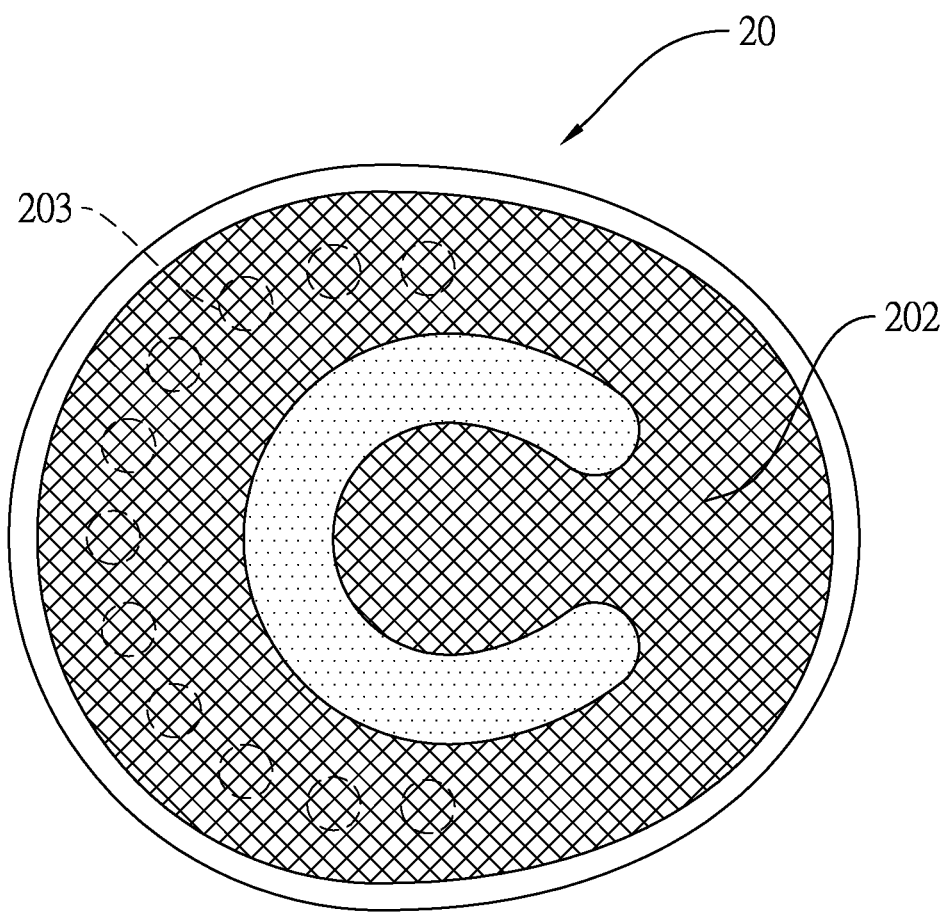
FIG. 6 is a front elevation view of the eyecup in FIG. 4.

With reference to FIG. 1 to FIG. 3, an eye mask for sleeping in accordance with the present invention is provided. The eye mask is configured to fix on a face of a user and thereby cover eyes of the user, which prevents the light from entering the eyes of the user.

The eye mask for sleeping comprises a headband 10 and two eyecups 20. The headband 10 is configured to be wound and fixed on a head of the user, and the two eyecups 20 are configured to cover the two eyes of the user, thereby preventing the light from entering the eyes of the user.

The headband 10 comprises an inner surface 101 and an outer surface 102. Each one of the eyecups 20 comprises a contact surface 201 and an adhering surface 202. The contact surface 201 of each one of the eyecups 20 is configured to contact and cover one of the eyes of the user. The adhering surface 202 of each one of the eyecups 20 is detachably securely mounted on the inner surface 101 of the headband 10. In other words, each one of the eyecups 20 is detachably but securely mounted on the headband 10. The inner surface 101 of the headband 10 faces toward the face of the user. The outer surface 102 is another surface of the headband 10 opposite the inner surface 101. The surfaces of the headband 10 and the two eyecups 20 are made of breathable fabric.

Figure 9:
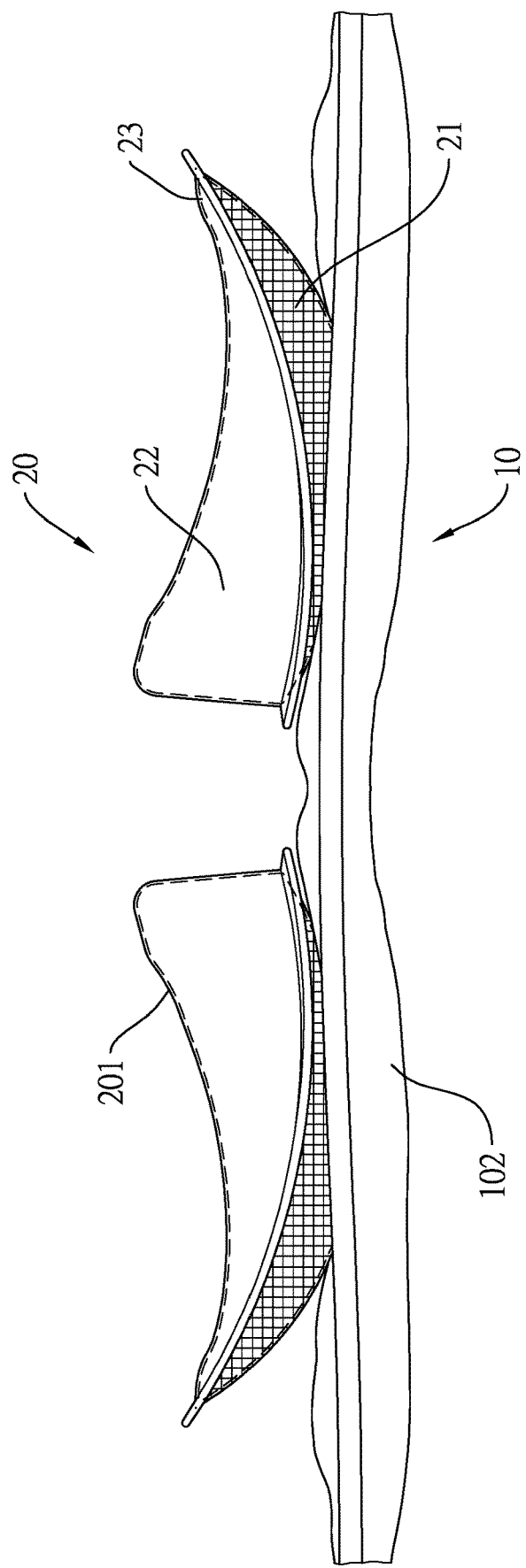
FIG. 9 is a bottom plan view of the eye mask in FIG. 1.

Then please refer to FIG. 3, FIG. 8, and FIG. 9. Each one of the eyecups 20 comprises a plurality of first passages 203. The first passages 203 are formed through the eyecup 20 and extend from the adhering surface 202 of the eyecup 20 to the contact surface 201 of the eyecup 20. The headband 10 comprises a plurality of second passages 103. The second passages 103 are formed through the headband 10 and extend from the inner surface 101 to the outer surface 102. Therefore, when the user wears the eye mask of the present invention, the sweat of the user can evaporate via the first passages 203 and drain out via the second passages 103. In another embodiment, the eyecup 20 may comprise the first passage 203 but the headband 10 does not have any second passage 103, which still can achieve a basic evaporation effect. The first passages 203 may be aligned to one of the second passages 103 and thereby the first passages 203 and the second passages 103 communicate with each other.

Then please refer to FIG. 3 to FIG. 6. Each one of the eyecups 20 may comprise a shading piece 21, a breathable cushion 22, and a shading pad 23. The shading piece 21 is made of opaque material and the adhering surface 202 of the eyecup 20 is formed on the shading piece 21. In other words, each one of the eyecups 20 is fixed on the headband 10 via the shading piece 21.

The breathable cushion 22 is securely mounted on a surface of the shading piece 21 and that surface is opposite the adhering surface 202. The breathable cushion 22 is C-shaped and the C-shaped breathable cushion 22 forms an opening. The opening is oriented toward an end of the headband 10. Therefore, the eyecup 20 has a recessed portion 204 enclosed by the C-shaped breathable cushion 22. In this embodiment, in a direction from a middle of the headband 10 to either end of the headband 10, a thickness of the breathable cushion 22 of each eyecup 20 is progressively decreased. In other words, the thickness thereof is progressively decreased from a middle of the C-shaped breathable cushion 22 to two ends of the C-shaped breathable cushion 22. The contact surface 201 of the eyecup 20 is formed on the breathable cushion 22 and the first passages 203 are formed through the breathable cushion 22.

The shading pad 23 is configured to contact the face of the user. Thus, the shading pad 23 may be part of the contact surface 201 of the eyecup 20. The shading pad 23 may be mounted on an end of the shading piece 21 and said end is near one of the ends of the headband 10. The shading pad 23 protrudes with respect to the shading piece 21. Precisely, the shading pad 23 may be mounted in the opening of the C-shaped breathable cushion 22. In this embodiment, the shading pad 23 may be a solid fabric pad; but, in another embodiment, the shading pad 23 may be an air cushion, which contains air therein.

Then please refer to FIG. 2 and FIG. 8. With the aforementioned structures, when the two eyecups 20 are mounted on the headband 10, thicker ends of the breathable cushions 22 of the two eyecups 20 contact two sides of the nose respectively and the shading pads 23 contact outer corners of eyes of the user. Because the recessed portion 204 of the eyecup 20 corresponds to the eyeball in position, the eye mask of the present invention can provide the most comfortable and oppression-free wearing experience for the user. Precisely, with the first passages 203 formed through the breathable cushion 22, heat and moisture can be dissipated and drained via the first passages 203, which decreases the chance of sweat accumulation between the skin and the eye mask. With the shading pad corresponding to the outer corner of the eye in location and protruding with respect to the shading piece 21, light may not penetrate into the eye mask, which prevents the eyes of the user from exposure to any light. Further, with the thickness of the breathable cushion 22 being thicker at the portion near the nose but thinner at the portion near the ear, even the user is used to sleep on the side, the eye mask of the present invention would not oppress the face of the user.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An eyecup of an eye mask for sleeping configured to cover one eye of a user, the eyecup comprising:
   an adhering surface;
   a contact surface configured to cover the eye of the user;
   a plurality of first passages formed through the eyecup of the eye mask for sleeping and extending from the adhering surface to the contact surface;
   a shading piece, the adhering surface formed on the shading piece;
   a breathable cushion securely mounted on a surface of the shading piece, said surface being opposite the adhering surface; the contact surface formed on the breathable cushion and the first passages formed through the breathable cushion; the breathable cushion being C-shaped and an opening of the C-shaped breathable cushion configured to be oriented toward an ear of the user; a thickness of the breathable cushion being progressively decreased from a middle of the C-shaped breathable cushion to two ends of the C-shaped breathable cushion; and
   a recessed portion enclosed by the breathable cushion.

2. The eyecup of an eye mask for sleeping as claimed in claim 1, wherein the thickness of the breathable cushion is configured to be progressively decreased in a direction from a nose of the user to the ear of the user.

3. The eyecup of an eye mask for sleeping as claimed in claim 2, further comprising:
   a shading pad mounted on an end of the shading piece, said end of the shading piece configured to be near the ear of the user, the shading pad protruding with respect to the shading piece and configured to contact a face of the user.

4. The eyecup of an eye mask for sleeping as claimed in claim 3, wherein the shading pad is an air cushion.

5. The eyecup of an eye mask for sleeping as claimed in claim 4, wherein:
   the shading pad is mounted in the opening of the C-shaped breathable cushion.

6. The eyecup of an eye mask for sleeping as claimed in claim 1 further comprising:
   a shading pad mounted in the opening of the C-shaped breathable cushion.

7. An eye mask for sleeping comprising:
   a headband having an inner surface and an outer surface; and
   two eyecups configured to respectively cover two eyes of a user; each one of the eyecups comprising:
     an adhering surface securely mounted on the inner surface of the headband;
     a contact surface configured to cover one of the eyes of the user;
     a plurality of first passages formed through the eyecup and extending from the adhering surface to the contact surface;
     a shading piece, the adhering surface formed on the shading piece;
     a breathable cushion securely mounted on a surface of the shading piece, said surface being opposite the adhering surface; the contact surface formed on the breathable cushion and the first passages formed through the breathable cushion; the breathable cushion being C-shaped and an opening of the C-shaped breathable cushion configured to be oriented toward an ear of the user; a thickness of the breathable cushion being progressively decreased from a middle of the C-shaped breathable cushion to two ends of the C-shaped breathable cushion; and
     a recessed portion enclosed by the breathable cushion.

8. The eye mask for sleeping as claimed in claim 7, wherein each one of the eyecups is detachably mounted on the headband.

9. The eye mask for sleeping as claimed in claim 7, wherein the headband comprises:
   a plurality of second passages formed through the headband and extending from the inner surface to the outer surface.

* * * * *